United States Patent
Ogasawara et al.

(10) Patent No.: US 9,199,902 B2
(45) Date of Patent: *Dec. 1, 2015

(54) EMULSIFIER FOR EMULSION POLYMERIZATION

(71) Applicant: Dai-Ichi Kogyo Seiyaku Co., Ltd., Kyoto (JP)

(72) Inventors: Asako Ogasawara, Kyoto (JP); Masayuki Hashimoto, Kyoto (JP)

(73) Assignee: Dai-Ichi Kogyo Seiyaku co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,280

(22) Filed: Jul. 9, 2014

(65) Prior Publication Data

US 2014/0323753 A1 Oct. 30, 2014

Related U.S. Application Data

(63) Continuation of application No. PCT/JP2013/000026, filed on Jan. 9, 2013.

(30) Foreign Application Priority Data

Jan. 16, 2012 (JP) .................................. 2012-006393
Jul. 11, 2012 (JP) .................................. 2012-155784

(51) Int. Cl.
| | | |
|---|---|---|
| C07C 309/24 | (2006.01) | |
| C07C 43/23 | (2006.01) | |
| C07C 59/13 | (2006.01) | |
| C07F 9/09 | (2006.01) | |
| C08F 2/26 | (2006.01) | |
| C08F 2/30 | (2006.01) | |
| C08G 65/26 | (2006.01) | |
| C07F 9/38 | (2006.01) | |

(52) U.S. Cl.
CPC ............ *C07C 43/23* (2013.01); *C07C 59/13* (2013.01); *C07C 309/24* (2013.01); *C07F 9/09* (2013.01); *C07F 9/3808* (2013.01); *C08F 2/26* (2013.01); *C08F 2/30* (2013.01); *C08G 65/2612* (2013.01); *C08G 65/2615* (2013.01); *C08G 65/2636* (2013.01); *C08G 65/2639* (2013.01)

(58) Field of Classification Search
CPC ...... C07C 309/24; C07C 43/23; C07C 59/13; C07F 9/09; C07F 9/3808; C08F 2/26; C08F 2/30; C08G 65/2612; C08G 65/2615; C08G 65/2636; C08G 65/2639
See application file for complete search history.

(56) References Cited

U.S. PATENT DOCUMENTS

| | | |
|---|---|---|
| 4,918,211 A | 4/1990 | Yokota et al. |
| 5,332,854 A | 7/1994 | Yokota et al. |

FOREIGN PATENT DOCUMENTS

| | | |
|---|---|---|
| JP | 56-161403 | 12/1981 |
| JP | 62-100502 | 5/1987 |
| JP | 62-221431 | 9/1987 |
| JP | 62-221432 | 9/1987 |
| JP | 63-183998 | 7/1988 |
| JP | 63-319035 | 12/1988 |
| JP | 4-50204 | 2/1992 |
| JP | 4-53802 | 2/1992 |
| JP | 4-55401 | 2/1992 |
| JP | 6-248005 | 9/1994 |
| JP | 10-316611 | 12/1998 |
| JP | 11-71340 | 3/1999 |

OTHER PUBLICATIONS

Miller et al. (J. Org. Chem. (1982), 47(4), 710-719).*

* cited by examiner

*Primary Examiner* — Valerie Rodriguez-Garcia
(74) *Attorney, Agent, or Firm* — Jordan and HamburgLLP

(57) ABSTRACT

An emulsifier for emulsion polymerization contains a compound represented by the following general formula (I).

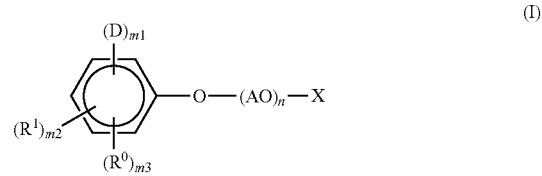

8 Claims, No Drawings

EMULSIFIER FOR EMULSION POLYMERIZATION

REFERENCE TO RELATED APPLICATION

This is a continuation of PCT International Application No. PCT/JP2013/000026 filed Jan. 9, 2013. The subject matter of the aforementioned prior application is hereby incorporated herein by reference.

TECHNICAL FIELD

The present invention relates to an emulsifier to be used in an emulsion polymerization step, more particularly relates to an emulsifier for emulsion polymerization, which can enhance the stability of a polymer dispersion, and also enhance the physical properties of a polymer film obtained from the polymer dispersion.

BACKGROUND ART

Heretofore, as emulsifiers for emulsion polymerization, anionic surfactants such as soaps, sodium dodecylbenzene sulfonate, polyoxyethylene alkyl phenyl ether sulfate ester salts, and polyoxyethylene alkyl ether sulfate ester salts; and nonionic surfactants such as polyoxyethylene nonyl phenyl ethers and polyoxyethylene alkyl ethers have been used. However, a polymer film obtained from a polymer dispersion using any of the above emulsifiers has problems that the emulsifier used remains in a free form in the polymer film, and therefore, the water resistance and the adhesiveness of the film are poor, etc. Therefore, as measures for the problems, a lot of reactive emulsifiers having a copolymerizable unsaturated group have been proposed (for example, PTL 1 to PTL 3).

A reactive emulsifier having an acrylic group or a methacrylic group as a copolymerizable unsaturated group, which has been proposed in the prior art, has high copolymerizability with a monomer, but has a problem that the polymerization stability during emulsion polymerization is deteriorated. For example, agglomerates during emulsion polymerization are increased, particles formed by emulsion polymerization are coarse and have poor stability over time, and so on. A reactive emulsifier having an allyl group as a copolymerizable unsaturated group sometimes has poor copolymerizability between the reactive emulsifier and a monomer depending on the type of the monomer or the polymerization conditions. Also a polymer film obtained from a polymer dispersion has a problem which remains unsolved that a film having quite satisfactory water resistance and adhesiveness cannot be obtained or a processing trouble is caused due to foaming in the polymer dispersion. In particular, in the case where styrene is contained as a monomer during emulsion polymerization, the above-described problems often occur, and it has been strongly demanded to relieve these problems in the commercial production.

CITATION LIST

Patent Literature

PTL 1: JP-A-63-183998
PTL 2: JP-A-63-319035
PTL 3: JP-A-04-050204

SUMMARY OF INVENTION

Technical Problem

The present invention has been made in view of the above-described circumstances and has an object to provide a reactive emulsifier for emulsion polymerization, with which the polymerization stability during emulsion polymerization is made more favorable, the foaming problem is solved, and the properties such as water resistance and adhesiveness of a polymer film obtained from a polymer dispersion after the polymerization can be significantly improved. Further, the present invention has an object to provide a reactive emulsifier for emulsion polymerization, with which the properties of the obtained polymer dispersion can be significantly improved even in the case where styrene is contained as a monomer, which is particularly problematic in the commercial production as described above.

Solution to Problem

In order to achieve the above-described objects, the emulsifier for emulsion polymerization of the present invention contains a compound represented by the following formula (I):

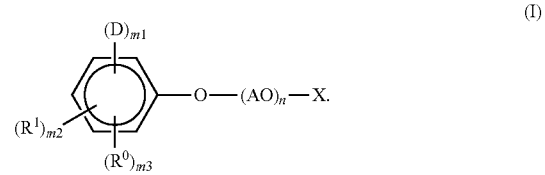

In formula (I), $R^0$ represents an alkyl group having 1 to 4 carbon atoms, $R^1$ is independently selected from one or more of the groups shown below, $R^2$ represents hydrogen or a methyl group, D represents a polymerizable unsaturated group represented by the chemical formula D-1 or the chemical formula D-2, $R^3$ represents a hydrogen atom or a methyl group, m1 is an integer that is 1 or 2, m2 is an integer that is 1, 2 or 3, m3 is an integer that is 0 or 1, A represents an alkylene group or a substituted alkylene group having 2 to 4 carbon atoms, n represents an average addition mole number of alkylene oxide and represents a number in the range of 0 to 1,000, X represents a hydrogen atom or an anionic hydrophilic group selected from $-(CH_2)_a-SO_3M$, $-(CH_2)_b-COOM$, $-PO_3M_2$, $-P(Z)O_2M$, and $-CO-CH_2-CH(SO_3M)-COOM$, wherein a and b each represent an integer of 0 to 4, Z represents a residue obtained by removing X from the general formula (I), and each M represents a hydrogen atom, an alkali metal atom, an alkaline earth metal atom, an ammonium residue, or an alkanolamine residue.

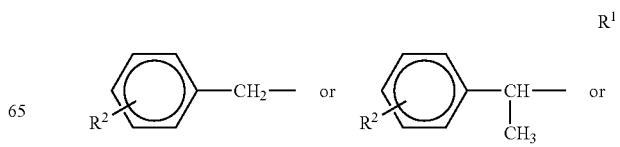

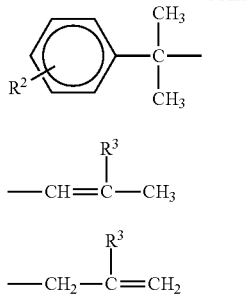

D-1

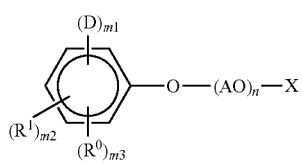

D-2

The emulsifier for emulsion polymerization, when a mixture of compounds, m1 has as an average valuem1avg that is a number in the following range: 1<m1avg<1.5, and the molar ratio of the group D-1 to the group D-2, expressed as (D-1)/(D-2), is larger than 2.

Further, as the emulsifier, one configured such that in the general formula (I), X represents a hydrogen atom or $SO_3M$, wherein M represents a hydrogen atom, an alkali metal atom, an alkaline earth metal atom, an ammonium residue, or an alkanolamine residue, and A represents an alkylene group having 2 carbon atoms can be preferably used.

Advantageous Effects of Invention

According to the present invention, an emulsifier for emulsion polymerization, with which the stability during emulsion polymerization is enhanced, the foaming problem is relieved, and the properties such as water resistance and adhesiveness of a polymer film obtained from a polymer dispersion are significantly enhanced can be provided.

DESCRIPTION OF EMBODIMENTS

Hereinafter, embodiments of the present invention will be described. The emulsifier for emulsion polymerization of the present invention contains, as a main component, a compound represented by the following general formula (I) as described above.

$$(D)_{m1}\text{-Ar}(R^1)_{m2}(R^0)_{m3}-O-(AO)_n-X \quad (I)$$

In formula (I), $R^0$ represents an alkyl group having 1 to 4 carbon atoms, $R^1$ is independently selected from one or more of the groups shown below, $R^2$ represents hydrogen or a methyl group, D represents a polymerizable unsaturated group represented by the chemical formula D-1 or the chemical formula D-2, $R^3$ represents a hydrogen atom or a methyl group, m1 is an integer that is 1 or 2, m2 is an integer that is 1, 2 or 3, m3 is an integer that is 0 or 1, and the sum of m1, m2, and m3 is 2 to 5. When the number of the D groups or the $R^1$ groups is more than 1, the D groups or the $R^1$ groups may be the same as or different from one another. A represents an alkylene group or a substituted alkylene group having 2 to 4 carbon atoms, n represents an average addition mole number of alkylene oxide and represents a number in the range of 0 to 1,000, X represents a hydrogen atom or an anionic hydrophilic group selected from $-(CH_2)_a-SO_3M$, $-(CH_2)_b-COOM$, $-PO_3M_2$, $-P(Z)O_2M$, and $-CO-CH_2-CH(SO_3M)-COOM$, wherein a and b each represent an integer of 0 to 4, Z represents a residue obtained by removing X from the general formula (I), and each M represents a hydrogen atom, an alkali metal atom, an alkaline earth metal atom, an ammonium residue, or an alkanolamine residue.

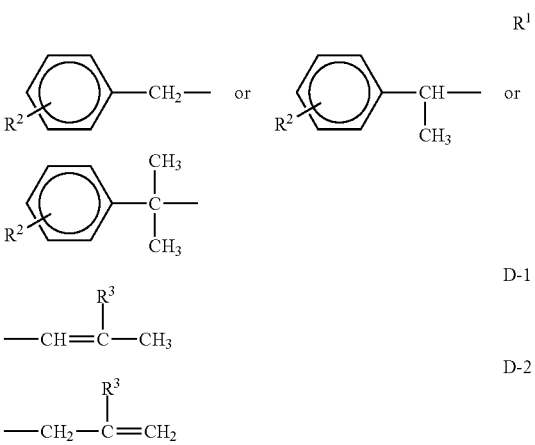

As described above, since $R^3$ in the chemical formulae D-1 and D-2 represents a hydrogen atom or a methyl group, D specifically represents a 1-propenyl group, a 2-methyl-1-propenyl group, or a allyl (or methallyl) group. One or more selected from these 1-propenyl group, 2-methyl-1-propenyl group, and allyl (or methallyl) group represented by D may be present in a molecule. However, D is preferably a 1-propenyl group. Further, m1 which represents the number of substituents represented by the above-described D is a number of 1 or more, preferably a number of 1 to 2, and the position of substitution for D is preferably an ortho position (2- or 6-position). Further, when the emulsifier for emulsion polymerization is a mixture of compounds, m1 preferably has an average valuem1avg that is a number in the following range: 1<m1avg <1.5, and the molar ratio of the group D-1 to the group D-2, expressed as (D-1)/)D-2, is preferably larger than 2.

Further, the (AO)n chain moiety in the general formula (I) can be obtained by selecting one or more types of alkylene oxides having 2 to 4 carbon atoms from ethylene oxide, propylene oxide, butylene oxide, and tetrahydrofuran (1,4-butylene oxide), followed by addition polymerization of them. The form of the polymerization of the alkylene oxide and the like to be added is not limited and may be a homopolymer of one type of alkylene oxide, a random copolymer or a block copolymer of two or more types of alkylene oxides, or a combination of the random adduct with the block copolymer.

As the alkylene oxide, an oxyethylene group is particularly preferable. In the case where two or more types of alkylene oxides are selected, it is preferable to select ethylene oxide as one type, and the (AO)n chain moiety is a (poly)oxyalkylene chain containing an oxyethylene group in an amount of preferably from 50 to 100 mol %, more preferably from 70 to 100 mol %.

The degree of polymerization n represents the average addition mole number of alkylene oxide and is a number in the range of 0 to 1,000, preferably a number in the range of 0 to 100. More specifically, in the case where X in the general formula (I) is a hydrogen atom, the degree of polymerization n is preferably a number in the range of 10 to 50. Further, in the case where X is an ionic hydrophilic group, the degree of polymerization n is preferably a number in the range of 0 to 50, more preferably a number in the range of 3 to 30.

In the emulsifier for emulsion polymerization employed in the present invention represented by the general formula (I), the content and the degree of polymerization n of the oxyethylene group in the (AO)n chain can vary the degree of hydrophilicity or hydrophobicity of the emulsifier, and it is preferable to appropriately design the composition of the (AO) n chain moiety according to the properties of a desired polymer dispersion or the properties of a desired polymer film of the present invention, or the monomer to be used or the intended use of them.

X in the general formula (I) is a hydrogen atom or an anionic hydrophilic group represented by —$(CH_2)_a$—$SO_3M$, —$(CH_2)_b$—COOM, —$PO_3M_2$, —$P(Z)O_2M$, or —CO—$CH_2$—CH($SO_3M$)-COOM, (wherein a and b each represent an integer of 0 to 4, Z represents a residue obtained by removing X from the above-described general formula (I)), or the like. In the formula representing the above-described anionic hydrophilic group, M represents a hydrogen atom, an alkali metal atom such as lithium, sodium, or potassium, an alkaline earth metal atom such as magnesium or calcium, ammonium, or an alkanolamine residue. Examples of the ammonium include ammonium of ammonia and ammonium of an alkylamine such as monomethylamine or dipropylamine, and examples of the alkanolamine residue include a monoethanolamine residue, a diethanolamine residue, and a triethanolamine residue. Among these anionic hydrophilic groups, a group represented by —$SO_3M$, —$PO_3M_2$, or —$P(Z)O_2M$ is preferable. Incidentally, —$PO_3M_2$ described above represents a monoester with a residue Z obtained by removing X from the general formula (I), and —$P(Z)O_2M$ represents a diester with a residue Z obtained by removing X from the general formula (I). As described above, these can be used in the present invention as a single composition or as a mixture.

Hereinafter, a series of steps of a method for producing the emulsifier for emulsion polymerization of the present invention will be described in detail. As a method for obtaining a phenol derivative, which has a polymerizable group in an aromatic ring, and is an intermediate of the emulsifier for emulsion polymerization of the present invention, (i) a method in which a phenol derivative having a substituent in an aromatic ring and an allyl halide are reacted with each other by a known method, followed by Claisen rearrangement in the presence of an alkali, whereby a phenol derivative having a polymerizable group in an aromatic ring is obtained, (ii) a method in which phenol and an allyl halide are reacted with each other by a known method, followed by Claisen rearrangement in the presence of an alkali, and then, introduction of a substituent into the aromatic ring under known conditions, whereby a phenol derivative having a polymerizable group in an aromatic ring is obtained, or the like is used. By using this compound as an intermediate, and then adding an alkylene oxide thereto, a desired nonionic emulsifier for emulsion polymerization can be obtained. Further, by introducing an ionic hydrophilic group into the nonionic compound using a known method, an emulsifier for emulsion polymerization having a desired ionic hydrophilic group can be obtained. Incidentally, in the present invention, the synthetic route is not particularly limited, and a method other than the above-described methods can also be used.

Hereinafter, a series of reaction steps will be described by showing a method for obtaining a target compound using a styrenated phenol as a starting material by way of example.

In the above-described general formula (I), the polymerizable unsaturated group represented by D is a 1-propenyl group, a 2-methyl-1-propenyl group, or an allyl (or methallyl) group as described above. Among these, an allyl (or methallyl) group is introduced by an allylation (or methallylation) reaction of a styrenated phenol. On the other hand, a 1-propenyl group or a 2-methyl-1-propenyl group can be introduced as follows. After an allylation (or methallylation) reaction of a styrenated phenol or a styrenated alkylphenol (hereinafter sometimes abbreviated as "styrenated (alkyl) phenol"), the allyl group is rearranged to a 1-propenyl group or a 2-methyl-1-propenyl group in the presence of an alkali. As the method for introducing a 1-propenyl group into a styrenated (alkyl)phenol, the following method will be described as an example, however, the present invention is not limited to this synthetic method. That is, an allyl halide and a styrenated (alkyl)phenol are reacted with each other along with a basic substance such as sodium hydroxide or potassium hydroxide, and then, the resulting compound is further heated to about 100° C., whereby an allyl styrenated (alkyl) phenol is obtained. At this stage, by adjusting the amounts of the allyl halide and the basic substance, a monosubstituted styrenated (alkyl)phenol having one allyl group as a substituent, a disubstituted styrenated (alkyl)phenol having two allyl groups as substituents, and the like can be obtained. Hereinafter, this reaction will be described in more detail with reference to the following general formulae. According to the following reaction formulae (i) and (ii), an allyl styrenated phenol is obtained.

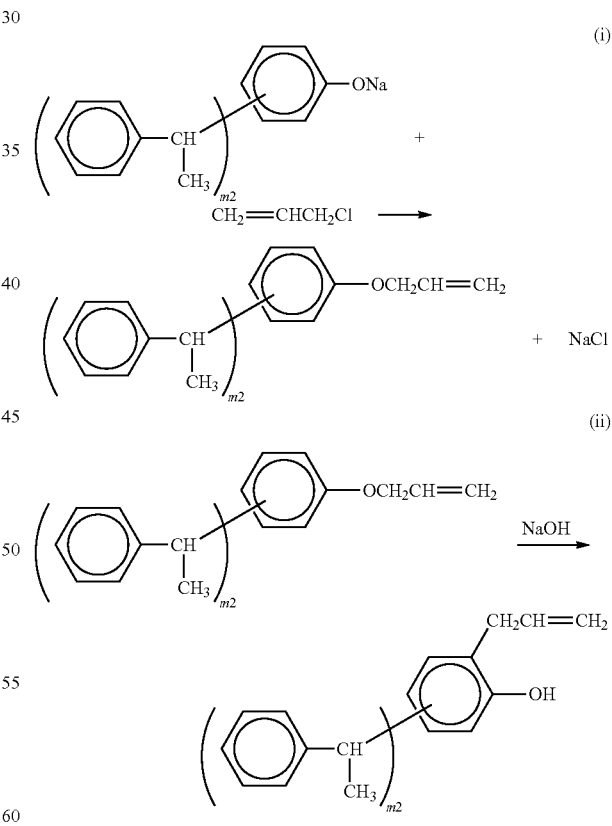

In addition, at this time, depending on the reaction conditions such as the charging ratio of the styrenated phenol to the allyl halide, the amount of a catalyst, or the reaction temperature, the reactions represented by the following reaction formulae (iii) and (iv) proceed to form a diallyl compound and the like as side products.

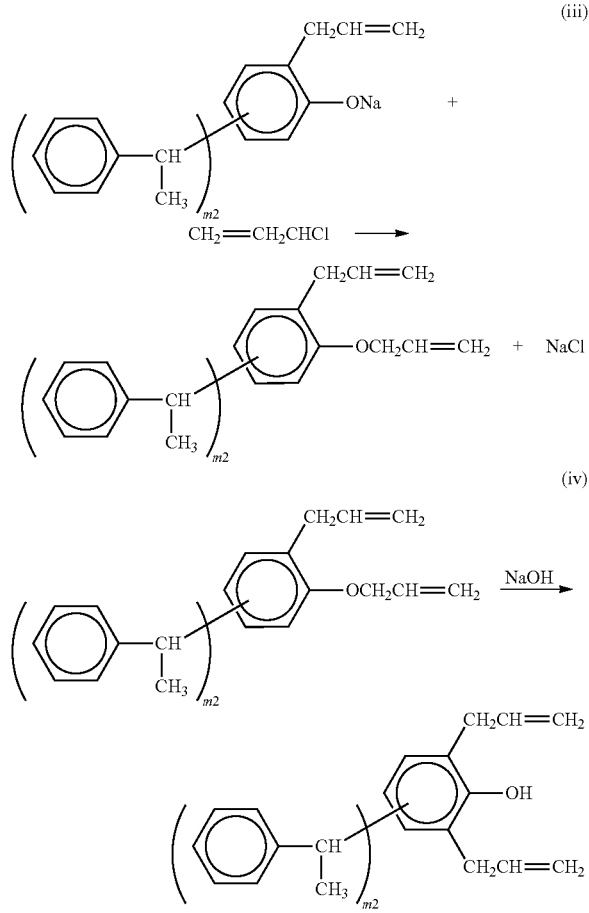

In this manner, according to the above-described reaction formulae (i) to (iv), a reaction composition containing a target (mono)allyl compound and also a diallyl compound and the like can be obtained. By heating such a reaction composition in the presence of an alkali hydroxide, the allyl group is rearranged to a 1-propenyl group, whereby a propenyl styrenated phenol, which is a main target product, is obtained. However, depending on the reaction conditions, a composition containing a given amount of an unrearranged allyl styrenated phenol can be obtained.

Hereinafter, the subsequent steps will be described by showing an allyl styrenated phenol obtained according to the above-described reaction formula (ii) by way of example. By adding a predetermined amount of an alkylene oxide to the obtained allyl styrenated phenol using a known method, a nonionic emulsifier for emulsion polymerization of the present invention, which is one of the target products, and in which D is a 1-propenyl group, m1 is 1, and X is a hydrogen atom in the general formula (I) is obtained as described above.

In the case where X in the general formula (I) is anionic hydrophilic group, a compound obtained by the above-described method is further subjected to a reaction of introducing an ionic hydrophilic group into the compound. The reaction conditions for introducing an anionic hydrophilic group represented by $-(CH_2)_a-SO_3M$ wherein a represents 0 among the formulae representing an ionic hydrophilic group are not particularly limited, and for example, the production can be achieved by reacting sulfamic acid, sulfuric acid, sulfuric anhydride, fuming sulfuric acid, chlorosulfonic acid, or the like. Further, the reaction conditions for introducing an anionic hydrophilic group represented by $-(CH_2)_a-SO_3M$ wherein a represents a number of 1 to 4 are also not particularly limited, and for example, the production can be achieved by reacting propane sultone, butane sultone, or the like.

The reaction conditions for introducing an anionic hydrophilic group represented by $-(CH_2)_b-COOM$ among the formulae representing an ionic hydrophilic group are also not particularly limited, and for example, the production can be achieved by oxidizing a hydroxyl group, or reacting a monohaloacetic acid to carry out carboxylation, or reacting acrylonitrile or acrylic acid ester, followed by saponification with an alkali.

The reaction conditions for introducing an anionic hydrophilic group represented by $-PO_3M_2$ and/or $-P(Z)O_2M$ (wherein Z represents a residue obtained by removing X from the general formula (I)) among the formulae representing an ionic hydrophilic group are also not particularly limited, and for example, the production can be achieved by reacting diphosphorus pentoxide, polyphosphoric acid, orthophosphoric acid, phosphorus oxychloride, or the like. In the case where a phosphate ester group is used as the anionic hydrophilic group, depending on the production method, a monoester compound and a diester compound are obtained as a mixture, and these compounds may be separated from each other, or may be directly used as a mixture. Further, the mixture can be used after it is subjected to a reaction in the presence of water to increase the content ratio of the monoester compound.

The reaction conditions for introducing an anionic group represented by $-CO-CH_2-CH(SO_3M)-COOM$ among the formulae representing an ionic hydrophilic group are also not particularly limited, and for example, the production can be achieved by reacting maleic anhydride to carry out monoesterification, and then, reacting anhydrous sodium sulfite to carry out sulfonation. Further, in the case where anionic hydrophilization is carried out, neutralization may be carried out thereafter with an alkali such as sodium hydroxide or potassium hydroxide, ammonia, an alkylamine, an alkanolamine such as monoethanolamine or diethanolamine, or the like.

[Monomer for Emulsion Polymerization]

The monomer to be applied to the emulsion polymerization using the emulsifier for emulsion polymerization of the present invention is not particularly limited, and it can be applied variously. For example, the monomer can be used for producing an acrylate-based emulsion, a styrene-based emulsion, a vinyl acetate-based emulsion, an SBR (styrene/butadiene) emulsion, an ABS (acrylonitrile/butadiene/styrene) emulsion, a BR (butadiene) emulsion, an IR (isoprene) emulsion, an NBR (acrylonitrile/butadiene) emulsion, or the like, and also, emulsion polymerization can be carried out by mixing two or more types of monomers.

Examples of the monomer constituting an acrylate-based emulsion include acrylic (or methacrylic) acid (ester)/acrylic (or methacrylic) acid (ester), acrylic (or methacrylic) acid (ester)/styrene, acrylic (or methacrylic) acid (ester)/vinyl acetate, acrylic (or methacrylic) acid (ester)/acrylonitrile, acrylic (or methacrylic) acid (ester)/butadiene, acrylic (or methacrylic) acid (ester)/vinylidene chloride, acrylic (or methacrylic) acid (ester)/allylamine, acrylic (or methacrylic) acid (ester)/vinylpyridine, acrylic (or methacrylic) acid (ester)/acrylic (or methacrylic) acid alkylolamide, acrylic (or methacrylic) acid (ester)/N,N-dimethylaminoethyl acrylate (or methacrylate), and acrylic (or methacrylic) acid (ester)/N,N-diethylaminoethyl vinyl ether.

Examples of the monomer constituting a styrene-based emulsion include, other than styrene alone, styrene/acrylonitrile, styrene/butadiene, styrene/fumaronitrile, styrene/maleinitrile, styrene/cyanoacrylate ester, styrene/phenylvinyl acetate, styrene/chloromethylstyrene, styrene/dichlorostyrene, styrene/vinyl carbazole, styrene/N,N-diphenylacrylamide, styrene/methylstyrene, acrylonitrile/butadiene/styrene, styrene/acrylonitrile/methylstyrene, styrene/acrylonitrile/vinyl carbazole, and styrene/maleic acid.

Examples of the monomer constituting a vinyl acetate-based emulsion include, other than vinyl acetate alone, vinyl acetate/styrene, vinyl acetate/vinyl chloride, vinyl acetate/acrylonitrile, vinyl acetate/maleic acid (ester), vinyl acetate/fumaric acid (ester), vinyl acetate/ethylene, vinyl acetate/propylene, vinyl acetate/isobutylene, vinyl acetate/vinylidene chloride, vinyl acetate/cyclopentadiene, vinyl acetate/crotonic acid, vinyl acetate/acrolein, and vinyl acetate/alkyl vinyl ether.

Examples of the monomer to be subjected to polymerization of a halogenated olefin-based monomer include vinyl chloride, vinylidene chloride, vinyl chloride/maleic acid (ester), vinyl chloride/fumaric acid (ester), vinyl chloride/vinyl acetate, vinyl chloride/vinylidene chloride, vinylidene chloride/vinyl acetate, and vinylidene chloride/vinyl benzoate.

Incidentally, when the monomers are expressed as "A/B" or the like as described above in this description, this notation indicates that these monomers in the group connected by a slash are used in combination.

[Emulsion Polymerization Conditions]

A polymerization initiator to be used in the emulsion polymerization reaction using the emulsifier for emulsion polymerization of the present invention is not particularly limited, and for example, hydrogen peroxide, ammonium persulfate, potassium persulfate, azobisisobutyronitrile, benzoyl peroxide, or the like can be used. As a polymerization accelerator, sodium hydrogen sulfite, ammonium ferrous sulfate, or the like can be used. Further, as a chain transfer agent, α-methylstyrene dimer, a mercaptan such as n-butylmercaptan, t-dodecylmercaptan, a halogenated hydrocarbon such as carbon tetrachloride or carbon tetrabromide, or the like may be used.

The use amount of the emulsifier of the present invention varies depending on the type of monomer or the like and is not limited to the following ranges, but in general, the use amount of them is preferably from 0.1 to 20 parts by mass, more preferably from 0.2 to 10.0 parts by mass with respect to 100 parts by mass of the total amount of the monomers.

The emulsifier for emulsion polymerization of the present invention can favorably complete the emulsion polymerization alone, however, within the range capable of achieving the effect of the present invention, an anionic surfactant or a cationic surfactant, or/and another nonionic surfactant may be used in combination. By doing this, the polymerization stability during emulsion polymerization is enhanced, and further, the treatment properties in the subsequent steps can be enhanced.

Such an anionic surfactant, a cationic surfactant, and a nonionic surfactant are not particularly limited. However, examples of the anionic surfactant include a fatty acid soap, a rosin acid soap, an alkyl sulfonate salt, an alkylaryl sulfonate salt, an alkyl sulfosuccinate salt, a polyoxyalkylene alkyl sulfate salt, and polyoxyalkylene aryl sulfate salt. Examples of the cationic surfactant include stearyl trimethyl ammonium, cetyl trimethyl ammonium, and lauryl trimethyl ammonium. Examples of the nonionic surfactant include polyoxyalkylene alkyl phenyl ether, polyoxyalkylene alkyl ether, alkyl polyglucoside, polyglycerin alkyl ether, polyoxyalkylene fatty acid ester, polyglycerin fatty acid ester, and sorbitan fatty acid ester.

As for the use amount of the surfactant to be used in combination, the surfactant is preferably contained in the emulsifier for emulsion polymerization of the present invention in an amount of 0.5 to 95% by mass, more preferably 5 to 60% by mass, further more preferably 10 to 30% by mass.

Further, for the purpose of enhancing the polymerization stability during emulsion polymerization, a known protective colloid agent can be used in combination. Examples of the protective colloid agent which can be used in combination include fully hydrolyzed polyvinyl alcohol, partially hydrolyzed polyvinyl alcohol, hydroxyethyl cellulose, carboxymethyl cellulose, methyl cellulose, polyacrylic acid, and gum Arabic.

As for another usage of the emulsifier for emulsion polymerization of the present invention, the emulsifier can be used by being added to the polymer after completion of polymerization for the purpose of improving the stability of the polymer emulsion. Further, the emulsifier for emulsion polymerization of the present invention can also be applied to suspension polymerization.

[Operation of Invention]

The emulsifier for emulsion polymerization of the present invention has a copolymerizable unsaturated group in a hydrophobic group moiety of its molecule, and therefore has excellent copolymerizability with a polymerizable monomer, particularly a styrene-based monomer, and is easily incorporated in the composition of a polymer. Therefore, the amount of the emulsifier present in a free form as a copolymerizable reactive emulsifier in a polymer film obtained from a polymer emulsion is significantly decreased, and therefore, an extremely excellent effect on the enhancement of the properties such as water resistance, adhesiveness, heat resistance, and weather resistance of the film is exhibited. Further, the foaming, the mechanical stability, and the like of the polymer emulsion are significantly improved.

EXAMPLES

Hereinafter, the present invention will be described in more detail with reference to Examples, however, it is to be construed that the present invention is not limited thereto. Incidentally, the proportions such as "%" as used herein are expressed in terms of mass unless otherwise specifically indicated. Further, in the structural formulae, "EO" represents an oxyethylene group, "PO" represents an oxypropylene group, and "BO" represents an oxybutylene group.

1. Synthesis Example of Compound Represented by General Formula (I)

Synthesis Example 1

In a reactor vessel equipped with a stirrer, a thermometer, and a reflux tube, 230 g (1.0 mol) of a styrenated phenol (a mixture of monostyrenated phenol:distyrenated phenol:tristyrenated phenol=72:27:1), 40 g (1.0 mol) of NaOH, and 210 g of acetone were charged, and the internal temperature was increased to 40° C. while stirring. Subsequently, 91 g (1.2 mol) of allyl chloride was added dropwise thereto over 1 hour. After completion of the dropwise addition, the temperature was maintained at 40° C. for an additional 2 hours to carry out a reaction. The reaction product was filtered to remove NaCl formed as a side product. Thereafter, acetone was removed under reduced pressure, whereby 314 g of allyl styrenated phenyl ether was obtained. This allyl phenyl ether was charged in an autoclave and kept stirred at 200° C. for 5 hours. At this stage, a rearrangement reaction occurred, whereby 2-allyl styrenated phenol was obtained. This 2-allyl styrenated phenol (290 g) was transferred to an autoclave, and 440 g (10 mol) of ethylene oxide was added thereto under the conditions that the pressure was 1.5 kg/cm³ and the temperature was 130° C. by using potassium hydroxide as a catalyst, whereby a crude product (mixture) containing a compound as follows (present invention product 1) represented by the general formula (I) at 99% was obtained. During this reaction, the allyl group was quantitatively converted to a 1-propenyl group.

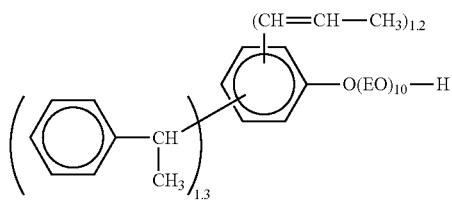

Synthesis Example 2

A compound as follows (present invention product 2) represented by the general formula (I) was obtained in the same manner as in the Synthesis Example 1 except that the amount of ethylene oxide was increased from 440 g (10 mol) to 2200 g (50 mol).

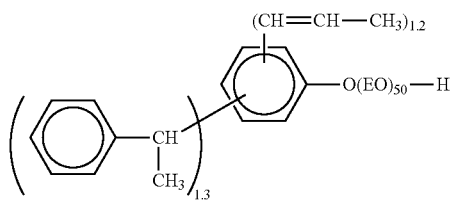

Synthesis Example 3

In a reactor vessel equipped with a stirrer, a thermometer, and a nitrogen inlet tube, 730 g (1 mol) of the compound (present invention product 1) obtained in the above-described Synthesis Example 1 was charged, and after replacing the atmosphere in the reactor with nitrogen, the compound was reacted with 97 g (1 mol) of sulfamic acid under the conditions of the temperature of 120° C., followed by purification, whereby a compound (present invention product 3) represented by the following general formula (I) was obtained.

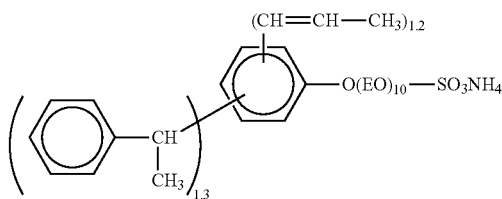

Synthesis Example 4

In a reactor vessel equipped with a stirrer and a thermometer, 730 g (1 mol) of the compound (present invention product 1) obtained in the Synthesis Example 1 was charged. Then, 128 g (1.1 mol) of sodium monochloroacetate and 44 g (1.1 mol) of sodium hydroxide were added to the reactor vessel whose internal temperature was set to 40° C. over 3 hours. Thereafter, while stirring at 40° C., the components were reacted with one another for 17 hours, followed by purification, whereby a compound as follows (present invention product 4) represented by the general formula (I) was obtained.

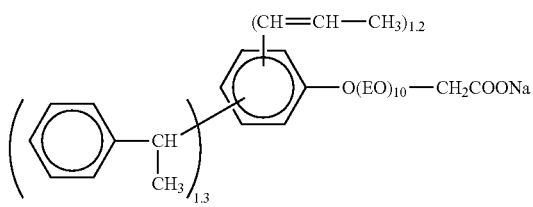

Synthesis Example 5

In a reactor vessel equipped with a stirrer and a thermometer, 730 g (1 mol) of the compound (present invention product 1) obtained in the Synthesis Example 1 was charged. Then, 94 g (0.33 mol) of phosphoric anhydride was charged therein while stirring, and phosphorylation was carried out at 80° C. for 5 hours while stirring. Thereafter, the reaction mixture was neutralized with sodium hydroxide, whereby a compound as follows (present invention product 5) represented by the general formula (I) was obtained. The thus obtained composition was confirmed by NMR, and it was found that the ratio of monoester to diester was 56/44.

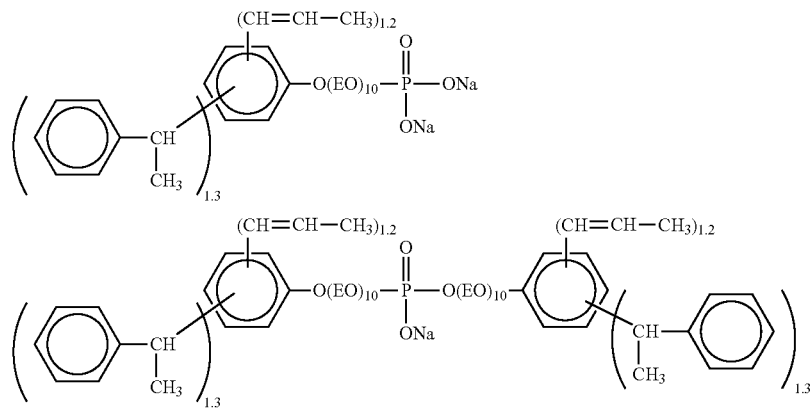

Synthesis Example 6

In a reactor vessel equipped with a stirrer, a thermometer, and a reflux tube, 300 g (1.0 mol) of 2-allyl styrenated phenol (a compound represented by the above general formula (I) wherein m2 is 1.5) was charged, and under the conditions that the pressure was 1.5 kg/cm$^3$ and the temperature was 130° C., 175 g (3 mol) of propylene oxide was added thereto, and then 440 g (10 mol) of ethylene oxide was added thereto by using potassium hydroxide as a catalyst. During this reaction, the allyl group was quantitatively converted to a 1-propenyl group. Further, 905 g (1 mol) of this propylene oxide-ethylene oxide block adduct was charged in a reactor vessel equipped with a stirrer, a thermometer, and a nitrogen inlet tube, and after replacing the atmosphere in the reactor with nitrogen, the compound was reacted with 97 g (1 mol) of sulfamic acid under the conditions of the temperature of 120° C., followed by purification, whereby a compound as follows (present invention product 6) represented by the general formula (I) was obtained.

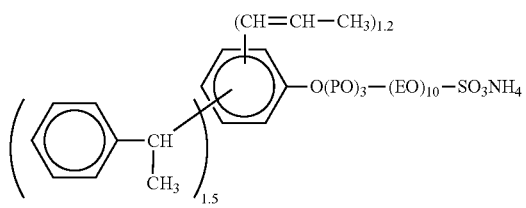

Synthesis Example 7

A compound as follows (present invention product 7) represented by the general formula (I) was obtained in the same manner as in the Synthesis Examples 1 and 3 except that the temperature during the addition reaction of ethylene oxide was changed from 130° C. to 115° C. The allyl group was converted to a 1-propenyl group during this reaction at a conversion ratio of 80%.

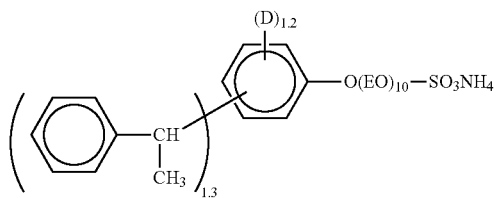

In the structural formula of the present invention product 7, D represents a 1-propenyl group and an allyl group, and the proportion of these groups is as follows in terms of molar ratio: 1-propenyl group/allyl group=80/20.

Synthesis Example 8

A compound as follows (present invention product 8) represented by the general formula (I) was obtained in the same manner as in the Synthesis Examples 1 and 3 except that the amount of allyl chloride was decreased from 91 g (1.2 mol) to 76 g (1.0 mol).

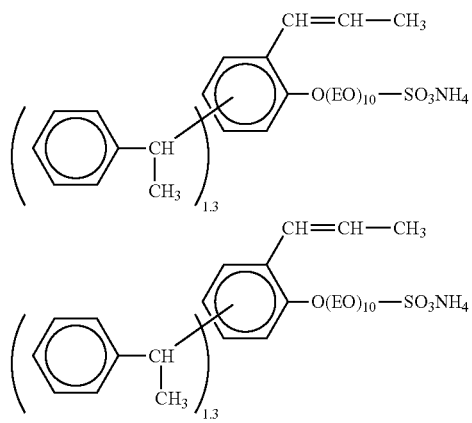

Synthesis Example 9

A compound as follows (present invention product 9) represented by the general formula (I) was obtained in the same manner as in the Synthesis Examples 1 and 3 except that a monostyrenated phenol was used in place of the mixture of distyrenated phenol and monostyrenated phenol, and the amount of allyl chloride was increased from 91 g (1.2 mol) to 152 g (2.0 mol).

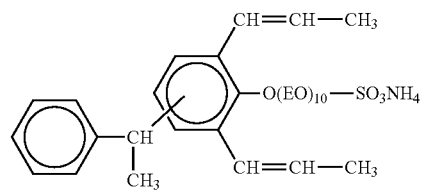

Synthesis Example 10

A compound as follows (present invention product 10) represented by the general formula (I) was obtained in the same manner as in the Synthesis Examples 1 and 3 except that cumylphenol was used in place of the mixture of distyrenated phenol and monostyrenated phenol.

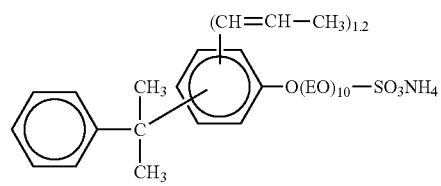

Synthesis Example 11

In a reactor vessel equipped with a stirrer, a thermometer, and a reflux tube, 253 g (1.0 mol) of a styrenated methylphenol (a mixture of monostyrenated methylphenol:distyrenated methylphenol:tristyrenated methylphenol=70:20:10), 40 g (1.0 mol) of NaOH, and 210 g of acetone were charged, and the internal temperature was increased to 40° C. while stirring. Subsequently, 91 g (1.2 mol) of allyl chloride was added dropwise thereto over 1 hour. After completion of the dropwise addition, the temperature was maintained at 40° C. for an additional 2 hours to carryout a reaction. The reaction product was filtered to remove NaCl formed as a side product. Thereafter, acetone was removed under reduced pressure, whereby 302 g of 2-allyl styrenated methyl phenyl ether was obtained. This 2-allyl styrenated methyl phenyl ether was charged in an autoclave and kept stirred at 200° C. for 5 hours. At this stage, a rearrangement reaction occurred, whereby 2-allyl styrenated methylphenol was obtained. This 2-allyl styrenated methylphenol with the amount of 302 g was transferred to an autoclave, and 440 g (10 mol) of ethylene oxide was added thereto under the conditions that the pressure was 1.5 kg/cm$^3$ and the temperature was 130° C. by using potassium hydroxide as a catalyst, whereby a crude product (mixture) containing a compound (present invention product 11) represented by the following formula with the ratio of 99% was obtained. During this reaction, the allyl group was quantitatively converted to a 1-propenyl group.

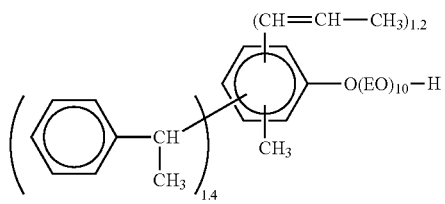

Synthesis Example 12

A compound (present invention product 12) represented by the following formula was obtained in the same manner as in the Synthesis Example 11 except that the amount of ethylene oxide was increased from 440 g (10 mol) to 2200 g (50 mol).

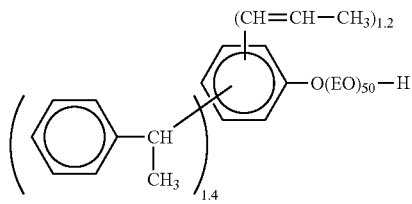

Synthesis Example 13

In a reactor vessel equipped with a stirrer, a thermometer, and a nitrogen inlet tube, 742 g (1 mol) of the compound (present invention product 11) obtained in the above-described Synthesis Example 11 was charged, and after replacing the atmosphere in the reactor with nitrogen, the compound was reacted with 97 g (1 mol) of sulfamic acid under the conditions of the temperature of 120° C., followed by purification, whereby a compound (present invention product 13) represented by the following formula was obtained.

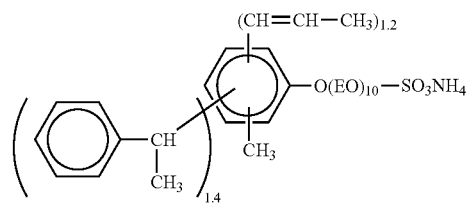

Synthesis Example 14

In a reactor vessel equipped with a stirrer and a thermometer, 742 g (1 mol) of the compound (present invention product 11) obtained in the Synthesis Example 11 was charged. Then, 128 g (1.1 mol) of sodium monochloroacetate and 44 g (1.1 mol) of sodium hydroxide were added to the reactor vessel whose internal temperature was set to 40° C. over 3 hours. Thereafter, while stirring at 40° C., the components were reacted with one another for 17 hours, followed by purification, whereby a compound (present invention product 14) represented by the following formula was obtained.

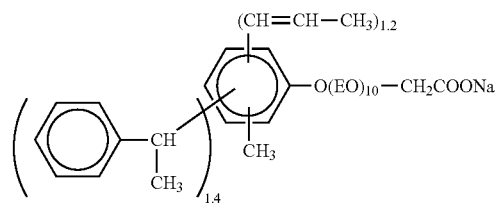

Synthesis Example 15

In a reactor vessel equipped with a stirrer and a thermometer, 742 g (1 mol) of the compound (present invention product 11) obtained in the Synthesis Example 11 was charged. Then, 94 g (0.33 mol) of phosphoric anhydride was charged therein while stirring, and phosphorylation was carried out at 80° C. for 5 hours while stirring. Thereafter, the reaction mixture was neutralized with sodium hydroxide, whereby a compound (present invention product 15) represented by the following formula was obtained. The thus obtained composition was confirmed by NMR, and it was found that the ratio of monoester to diester was 56/44.

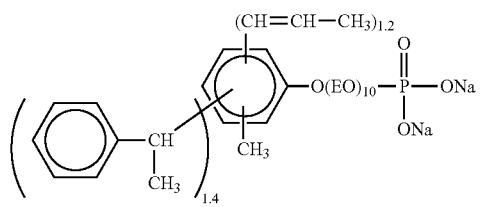

-continued

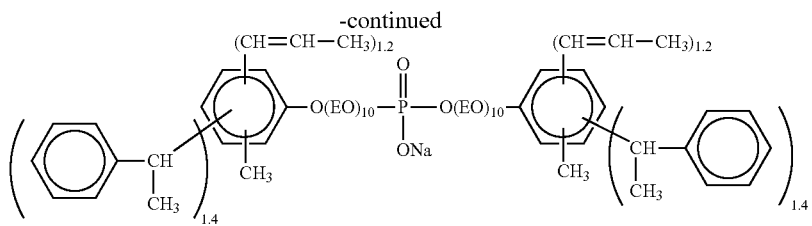

Synthesis Example 16

A compound (present invention product 16) represented by the following formula was obtained in the same manner as in the Synthesis Examples 11 and 13 except that the starting material was changed from styrenated methylphenol to a methyl styrenated methylphenol, and the amount of allyl chloride was increased from 91 g (1.2 mol) to 105 g (1.4 mol), and the amount of ethylene oxide was increased from 440 g (10 mol) to 880 g (20 mol).

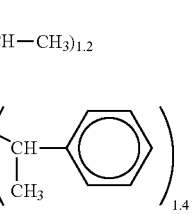

Synthesis Example 17

A compound (present invention product 17) represented by the following formula was obtained in the same manner as in the Synthesis Examples 11 and 13 except that the amount of allyl chloride was changed from 91 g (1.2 mol) to 75.8 g (1.0 mol).

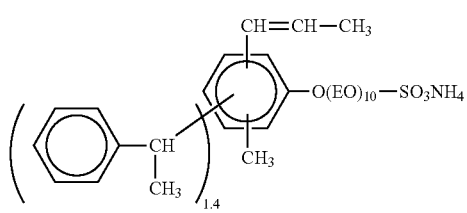

Further, the comparative products used for comparison in the following Use Examples are as follows.

Comparative Product 1

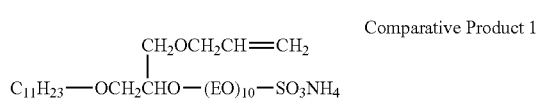

Comparative Product 2

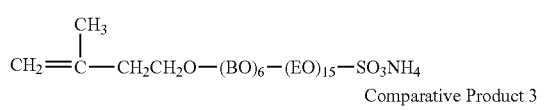

Comparative Product 3

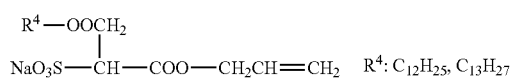

Comparative Product 4

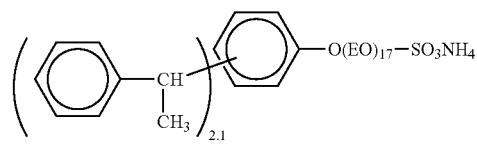

Comparative Product 5

$C_{12}H_{25}O-(EO)_{30}-SO_3NH_4$

Comparative Product 6

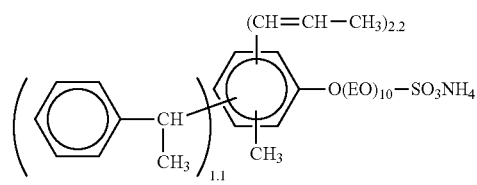

2. Use Example Emulsion Polymerization Agent

By using any of the emulsifiers for emulsion polymerization obtained in the above-described Synthesis Examples, emulsion polymerization was performed as described in the following Use Example, and with respect to the obtained polymer dispersions and polymer films, measurement and evaluation were performed. The measurement and evaluation methods used are as follows.

[Polymerization Stability]

The polymer dispersion was passed through an 80-mesh wire gauze to filter agglomerates formed during the emulsion polymerization step, and the filtration residue was washed with water and then dried at 105° C. for 2 hours. The mass of the dried residue was expressed in terms of "% by mass" relative to the solid content of the dispersion. Incidentally, in this measurement, a smaller amount of the agglomerates means that the polymerization stability in the emulsion polymerization step is higher.

[Average Particle Size]

A portion of the polymer dispersion was taken out and measured with respect to a particle size by using a dynamic light scattering particle size distribution analyzer (MICROTRAC UPA9340, manufactured by Nikkiso Co., Ltd.).

[Mechanical Stability]

50 g of the polymer dispersion was weighed out and treated at a load of 10 kg and at a number of revolutions of 1,000 rpm for 5 minutes by using a Marlon type tester, and formed agglomerates were filtered with an 80-mesh wire gauze. The residue was washed with water and then dried at 105° C. for 2 hours. The mass of the dried residue was expressed in terms of "% by mass" relative to the solid content of the dispersion. Incidentally, in this measurement, a smaller amount of the agglomerates means that the stability of the polymer dispersion under high shear conditions is higher.

[Foamability]

The polymer dispersion was diluted two-fold with water and a 30 mL aliquot was transferred to a 100-mL Nessler tube. Subsequently, the Nessler tube was inverted 30 times, and then left to stand for 5 minutes, and thereafter the amount (mL) of foam was measured.

[Water Whitening Resistance]

The polymer dispersion was coated to a film thickness of 120 μm (dry) on a commercially available glass plate and dried in an atmosphere of 20° C. and 65% RH for 24 hours. The resultant was dipped in ion-exchanged water at 25° C., and the glass plate was placed on 16-point printing letters. The letters were seen through the polymer film, and the number of days until the letters were no longer distinguishable was measured. The result was evaluated based on the following criteria.

A: The number of days was 21 or more.
B: The number of days was in the range of 11 to 20.
C: The number of days was in the range of 1 to 10.
D: The number of days was less than 1.

[Adhesive Holding Power]

The polymer dispersion obtained in the Use Example 2 was coated to a thickness of 25 μm (dry) on a PET film cut to a width of 5 cm, followed by a heat treatment. Thereafter, the resultant was attached to a SUS plate and pressure-bonded thereto by rolling. The film was partially peeled off so that the adhesion surface has a size of 5 cm×5 cm. Then, a 200-g weight was suspended from the edge of the film, and the time (sec) until the film was peeled off was measured. The result was evaluated based on the following criteria.

A: The time was 900 sec or more.
B: The time was 300 sec or more and less than 900 sec.
C: The time was less than 300 sec.

[Coefficient of Water Absorption]

The obtained polymer dispersion was coated to a film thickness of 120 μm (dry) on a commercially available glass plate and dried in an atmosphere of 20° C. and 65% RH for 24 hours. The polymer film was carefully peeled off from the glass plate, and the peeled polymer film was cut to a size of 5 cm×5 cm, and the mass (initial mass) of the polymer film was measured. Subsequently, this film was dipped in ion-exchanged water at 25° C., and 24 hours thereafter, the polymer film was taken out from the water. The water on the surface of the polymer film was lightly wiped off with a clean filter paper, and the mass (mass after dipping) of the polymer film was then measured. The coefficient of water absorption of the film was determined according to the following equation.

Coefficient of water absorption (% by mass)=[{(Mass of polymer film after dipping)−(Mass of polymer film before dipping)}/(Mass of polymer film before dipping)]×100

Use Example 1

Preparation of Styrene/Butyl Acrylate-Based Polymer Dispersion

As monomers, 123.75 g of styrene, 123.75 g of butyl acrylate, and 2.5 g of acrylic acid were used and mixed with 5.0 g of the emulsifier of the present invention product or the comparative product shown in Table 1 and 105 g of ion-exchanged water by using a homomixer, thereby preparing a mixed monomer emulsion. Aside from this, in a reactor equipped with a stirrer, a reflux condenser, a thermometer, a nitrogen inlet tube, and a dropping funnel, 122 g of ion-exchanged water and 0.25 g of sodium hydrogen carbonate were charged. A 36 g portion of the previously prepared mixed monomer emulsion described above was charged in the dropping funnel and added to the reactor all together, and then, the temperature was increased to 80° C. Thereafter, stirring was continued for 15 minutes. Subsequently, 0.5 g of ammonium persulfate as a polymerization initiator was dissolved in 20 g of ion-exchanged water, and the resulting solution was added to the reactor to initiate polymerization. Subsequently, 15 minutes after adding the polymerization initiator, 324 g of the rest of the mixed monomer emulsion was added dropwise thereto over 3 hours to carry out polymerization. Further, after maturation was allowed to proceed for consecutive 2 hours, the resultant was cooled and adjusted at a pH of 8 with ammonia water, whereby a polymer dispersion to be used for the evaluation experiments of the present invention was obtained.

The thus obtained polymer dispersion was evaluated for polymerization stability, average particle size, mechanical stability, and foamability, and also the polymer film was evaluated for water whitening resistance and coefficient of water absorption. The evaluation results are shown in Table 1.

Use Example 2

Preparation of 2-Ethylhexyl Acrylate/Butyl Acrylate-Based Polymer Dispersion

A polymer dispersion to be used for the evaluation experiments of the present invention was obtained by performing emulsion polymerization in the same manner as in the Use Example 1 except that among the monomer components in the above-described Use Example 1, styrene was changed to 2-ethylhexyl acrylate.

The thus obtained polymer dispersion was evaluated for polymerization stability, average particle size, mechanical stability, and foamability, and also the polymer film was evaluated for water whitening resistance and adhesive holding power. The evaluation results are shown in Table 2.

Use Example 3

Preparation of Styrene/Butyl Acrylate-Based Polymer Dispersion

As monomers, 123.75 g of styrene, 123.75 g of butyl acrylate, and 2.5 g of acrylic acid were used and mixed with 5.0 g of the emulsifier of the present invention product or the comparative product shown in Table 3 and 105 g of ion-exchanged water by using a homomixer, thereby preparing a mixed monomer emulsion. Aside from this, in a reactor equipped with a stirrer, a reflux condenser, a thermometer, a nitrogen inlet tube, and a dropping funnel, 122 g of ion-exchanged water and 0.25 g of sodium hydrogen carbonate were charged. A 36 g portion of the previously prepared mixed monomer emulsion described above was charged in the dropping funnel and added to the reactor all together, and then, the temperature was increased to 80° C. Thereafter, stirring was continued for 15 minutes. Subsequently, 0.5 g of ammonium persulfate as a polymerization initiator was dissolved in 20 g of ion-exchanged water, and the resulting solution was added to the reactor to initiate polymerization. Subsequently, 15 minutes after adding the polymerization initiator, 324 g of the rest of the mixed monomer emulsion was added dropwise to the reactor over 3 hours to carry out polymerization. Further, after maturation was allowed to proceed for consecutive 2 hours, the resultant was cooled and adjusted at a pH of 8 with ammonia water, whereby a polymer dispersion to be used for the evaluation experiments of the present invention was obtained.

The thus obtained polymer dispersion was evaluated for polymerization stability, average particle size, mechanical stability, and foamability, and also the polymer film was evaluated for water whitening resistance, and the coefficient of water absorption of them was measured. The evaluation results are shown in Table 3.

Use Example 4

Preparation of 2-Ethylhexyl Acrylate/Butyl Acrylate-Based Polymer Dispersion

A polymer dispersion to be used for the evaluation experiments of the present invention was obtained by performing emulsion polymerization in the same manner as in the Use Example 1 except that among the monomer components in the above-described Use Example 1, styrene was changed to 2-ethylhexyl acrylate.

The thus obtained polymer dispersion was evaluated for polymerization stability, average particle size, mechanical stability, and foamability, and also the polymer film was evaluated for water whitening resistance and adhesive holding power. The evaluation results are shown in Table 4.

TABLE 1

| | | Evaluation of polymer dispersion | | | | Evaluation of polymer film | |
| --- | --- | --- | --- | --- | --- | --- | --- |
| | Emulsifier | Polymerization stability (%) | Average particle size (μm) | Mechanical stability (%) | Foamability (ml) | Water whitening resistance | Coefficient of water absorption (%) |
| Use Example 1-1 | Present invention product 1/Present invention product 3 = 80/20 (mass ratio) | 0.11 | 0.33 | 0.24 | 8 | A | 5.5 |
| Use Example 1-2 | Present invention product 2/Present invention product 3 = 80/20 (mass ratio) | 0.14 | 0.30 | 0.20 | 7 | A | 5.3 |
| Use Example 1-3 | Present invention product 3 | 0.01 | 0.11 | 0.10 | 9 | A | 5.4 |
| Use Example 1-4 | Present invention product 3/Noigen XL-400[1]) = 80/20 (mass ratio) | 0.01 | 0.15 | 0.11 | 9 | A | 5.7 |
| Use Example 1-5 | Present invention product 4 | 0.06 | 0.13 | 0.13 | 10 | A | 5.2 |
| Use Example 1-6 | Present invention product 5 | 0.09 | 0.17 | 0.33 | 9 | A | 5.5 |
| Use Example 1-7 | Present invention product 6 | 0.10 | 0.15 | 0.25 | 12 | A | 5.0 |
| Use Example 1-8 | Present invention product 7 | 0.03 | 0.12 | 0.12 | 13 | A | 5.6 |
| Use Example 1-9 | Present invention product 8 | 0.02 | 0.14 | 0.11 | 11 | B | 7.5 |
| Use Example 1-10 | Present invention product 9 | 0.04 | 0.14 | 0.13 | 10 | A | 5.2 |
| Use Example 1-11 | Present invention product 10 | 0.07 | 0.12 | 0.15 | 11 | A | 5.4 |
| Comparative Use Example 1-1 | Comparative product 1 | 0.80 | 0.26 | 1.78 | 23 | C | 11.5 |
| Comparative Use Example 1-2 | Comparative product 2 | 3.50 | 0.77 | 5.22 | 26 | C | 13.5 |
| Comparative Use Example 1-3 | Comparative product 3 | 1.00 | 0.50 | 4.10 | 41 | C | 25.0 |
| Comparative Use Example 1-4 | Comparative product 4 | 0.24 | 0.18 | 0.12 | 57 | D | 35.0 |
| Comparative Use Example 1-5 | Comparative product 5 | 0.65 | 0.17 | 0.33 | 62 | D | 33.5 |

[1])polyoxyalkylene branched decyl ether, manufactured by Dai-Ichi Kogyo Seiyaku Co., Ltd.

TABLE 2

| | | Evaluation of polymer dispersion | | | | Evaluation of polymer film | |
| --- | --- | --- | --- | --- | --- | --- | --- |
| | Emulsifier | Polymerization stability (%) | Average particle size (μm) | Mechanical stability (%) | Foamability (ml) | Water whitening resistance | Adhesive holding power |
| Use Example 2-1 | Present invention product 2/Present invention product 3 = 80/20 (mass ratio) | 0.10 | 0.34 | 0.28 | 6 | A | A |
| Use Example 2-2 | Present invention product 3 | <0.01 | 0.12 | 0.10 | 7 | A | A |
| Use Example 2-3 | Present invention product 5 | 0.07 | 0.15 | 0.26 | 8 | A | A |
| Use Example 2-4 | Present invention product 6 | 0.05 | 0.15 | 0.20 | 10 | A | A |
| Use Example 2-5 | Present invention product 9 | 0.02 | 0.11 | 0.14 | 7 | A | A |
| Comparative Use Example 2-1 | Comparative product 1 | 0.29 | 0.20 | 0.58 | 39 | B | C |
| Comparative Use Example 2-2 | Comparative product 2 | 0.37 | 0.21 | 2.03 | 36 | C | C |
| Comparative Use Example 2-3 | Comparative product 4 | 0.10 | 0.13 | 0.31 | 48 | D | B |

TABLE 3

|  | Emulsifier | Polymerization stability (%) | Average particle size (μm) | Mechanical stability (%) | Foamability (ml) | Water whitening resistance | Coefficient of water absorption (%) |
|---|---|---|---|---|---|---|---|
| Use Example 3-1 | Present invention product 11/Present invention product 13 = 80/20 (mass ratio) | 0.15 | 0.32 | 0.26 | 9 | A | 5.7 |
| Use Example 3-2 | Present invention product 12/Present invention product 13 = 80/20 (mass ratio) | 0.14 | 0.34 | 0.14 | 6 | A | 5.6 |
| Use Example 3-3 | Present invention product 13 | <0.01 | 0.12 | 0.09 | 6 | A | 5.2 |
| Use Example 3-4 | Present invention product 14 | 0.04 | 0.15 | 0.10 | 10 | A | 5.8 |
| Use Example 3-5 | Present invention product 15 | 0.11 | 0.16 | 0.30 | 8 | A | 5.0 |
| Use Example 3-6 | Present invention product 16 | 0.08 | 0.20 | 0.28 | 7 | A | 5.3 |
| Use Example 3-7 | Present invention product 17 | 0.07 | 0.14 | 0.10 | 7 | B | 7.6 |
| Comparative Use Example 3-1 | Comparative product 1 | 0.80 | 0.26 | 1.78 | 23 | C | 10.5 |
| Comparative Use Example 3-2 | Comparative product 2 | 3.50 | 0.77 | 5.22 | 26 | C | 13.0 |
| Comparative Use Example 3-3 | Comparative product 3 | 1.00 | 0.50 | 4.10 | 41 | C | 27.5 |
| Comparative Use Example 3-4 | Comparative product 4 | 0.24 | 0.18 | 0.12 | 57 | D | 32.0 |
| Comparative Use Example 3-5 | Comparative product 5 | 0.65 | 0.17 | 0.33 | 62 | D | 34.7 |
| Comparative Use Example 3-6 | Comparative product 6 | 0.20 | 0.19 | 0.24 | 10 | C | 29.0 |

TABLE 4

|  | Emulsifier | Polymerization stability (%) | Average particle size (μm) | Mechanical stability (%) | Foamability (ml) | Water whitening resistance | Adhesive holding power |
|---|---|---|---|---|---|---|---|
| Use Example 4-1 | Present invention product 12/Present invention product 13 = 80/20 (mass ratio) | 0.10 | 0.31 | 0.27 | 8 | A | A |
| Use Example 4-2 | Present invention product 13 | <0.01 | 0.13 | 0.06 | 6 | A | A |
| Use Example 4-3 | Present invention product 15 | 0.08 | 0.16 | 0.19 | 7 | A | A |
| Comparative Use Example 4-1 | Comparative product 1 | 0.29 | 0.20 | 0.58 | 39 | B | C |
| Comparative Use Example 4-2 | Comparative product 2 | 0.37 | 0.21 | 2.03 | 36 | C | C |
| Comparative Use Example 4-3 | Comparative product 4 | 0.10 | 0.13 | 0.31 | 48 | D | B |

INDUSTRIAL APPLICABILITY

A polymer dispersion obtained by adding the emulsifier for emulsion polymerization of the present invention can be applied as, for example, an adhesive, a bonding agent, a coating agent, an impregnation enhancing agent, or the like, to resins, metals, papers, woods, cloths, and also to concretes, and the like. Further, the polymer dispersion or a solid polymer taken out from the polymer dispersion can be used in a modifier for resins, rubbers, and polymers.

The invention claimed is:

1. An emulsifier for emulsion polymerization, comprising a compound represented by formula (I):

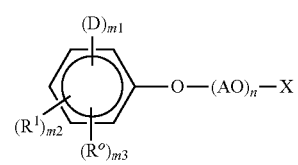

$R^0$ represents an alkyl group having 1 to 4 carbon atoms, $R^1$ is independently selected from one or more of the groups shown below, $R^2$ represents hydrogen or a methyl group:

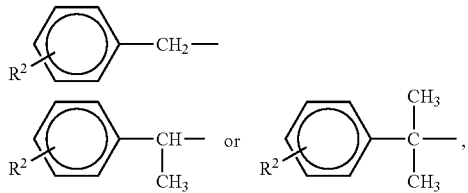

D represents a polymerizable unsaturated group represented by the chemical formula D-1 or the chemical formula D-2, $R^3$ represents a hydrogen atom or a methyl group:

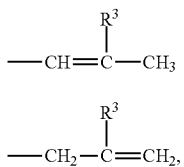

m1 is an integer that is 1 or 2, m2 is an integer that is 1, 2 or 3, m3 is an integer that is 0 or 1, X represents a hydrogen atom or an anionic hydrophilic group selected from —$(CH_2)_a$—$SO_3M$, —$(CH_2)_b$—COOM, —$PO_3M_2$, —$P(Z)O_2M$, and —CO—$CH_2$—$CH(SO_3M)$-COOM, wherein a and b each represent an integer of 0 to 4, Z represents a residue obtained by removing X from the general formula (I), and each M represents a hydrogen atom, an alkali metal atom, an alkaline earth metal atom, an ammonium residue, or an alkanolamine residue, and A represents an alkylene group or a substituted alkylene group having 2 to 4 carbon atoms, n represents an average addition mole number in the range of 10 to 1000 when X is hydrogen and an average addition mole number of 3 to 1000 when X is an ionic hydrophilic group.

2. The emulsifier for emulsion polymerization according to claim 1, wherein in the general formula (I), X represents a hydrogen atom or $SO_3M$, wherein M represents a hydrogen atom, an alkali metal atom, an alkaline earth metal atom, an ammonium residue, or an alkanolamine residue, and A represents an alkylene group having 2 carbon atoms.

3. The emulsifier for emulsion polymerization according to claim 1, wherein, when X is hydrogen, n is in the range of 10 to 100.

4. The emulsifier for emulsion polymerization according to claim 1, wherein, when X is an ionic hydrophilic group, n is in the range of 3 to 100.

5. The emulsifier for emulsion polymerization according to claim 1, wherein, when X is an ionic hydrophilic group, n is in the range of 3 to 50.

6. The emulsifier for emulsion polymerization according to claim 1, wherein, when X is hydrogen, n is in the range of 10 to 50.

7. The emulsifier for emulsion polymerization according to claim 1, wherein, when X is an ionic hydrophilic group, n is in the range of 3 to 30.

8. The emulsifier for emulsion polymerization according to claim 1, wherein $R^1$ is

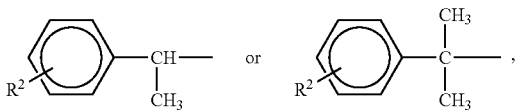

and $R^2$ is as defined in claim 1.

* * * * *